US 6,629,598 B2

(12) United States Patent
Narula et al.

(10) Patent No.: US 6,629,598 B2
(45) Date of Patent: Oct. 7, 2003

(54) FLEXIBLE RIBBED SPLINT SYSTEM

(76) Inventors: Vinod K. Narula, 9805 Silky Dogwood Ct., Louisville, KY (US) 40241; Dipak Narula, 9428 Wessex Pl., Louisville, KY (US) 40222

(*) Notice: Subject to any disclaimer, the term of this patent is extended or adjusted under 35 U.S.C. 154(b) by 0 days.

(21) Appl. No.: 10/216,946

(22) Filed: Aug. 12, 2002

(65) Prior Publication Data
US 2003/0032906 A1 Feb. 13, 2003

Related U.S. Application Data
(60) Provisional application No. 60/311,321, filed on Aug. 10, 2001.

(51) Int. Cl.[7] .................................................. A61F 5/04
(52) U.S. Cl. ............................................. 206/5; 206/21
(58) Field of Search ............................ 602/21–27, 5, 602/12

(56) References Cited

U.S. PATENT DOCUMENTS

| | | | | |
|---|---|---|---|---|
| 1,259,510 A | * | 3/1918 | Gorney | 602/4 |
| 1,741,011 A | * | 12/1929 | Carvill | 602/5 |
| 3,832,997 A | * | 9/1974 | Cappelletti | 602/11 |
| 4,055,171 A | * | 10/1977 | Ries | 602/22 |
| 4,088,129 A | * | 5/1978 | DiGiulio | 602/23 |
| 4,373,517 A | * | 2/1983 | Criscuolo | 602/5 |
| 4,776,326 A | * | 10/1988 | Young et al. | 602/16 |
| 5,385,536 A | * | 1/1995 | Burkhead et al. | 602/20 |
| 5,487,724 A | * | 1/1996 | Schwenn | 602/20 |
| 5,537,719 A | * | 7/1996 | Freed | 24/16 PB |
| 5,643,186 A | * | 7/1997 | Chinchalkar | 602/32 |
| 5,653,680 A | * | 8/1997 | Cruz | 602/21 |
| 5,709,648 A | * | 1/1998 | Webb | 602/19 |
| 5,713,837 A | * | 2/1998 | Grim et al. | 602/6 |
| 5,749,841 A | * | 5/1998 | Moore | 602/21 |
| 5,820,577 A | * | 10/1998 | Taylor | 601/40 |
| 5,839,124 A | * | 11/1998 | Tilton | 2/170 |
| 5,893,366 A | * | 4/1999 | Odell et al. | 128/869 |
| 6,063,087 A | * | 5/2000 | Agee et al. | 606/55 |
| 6,093,162 A | * | 7/2000 | Fairleigh et al. | 602/22 |
| 6,102,878 A | * | 8/2000 | Nguyen | 602/5 |
| 6,106,492 A | * | 8/2000 | Darcey | 602/8 |
| 6,206,846 B1 | * | 3/2001 | Kenney | 602/17 |
| 6,342,043 B1 | * | 1/2002 | Gottsmann et al. | 602/12 |

FOREIGN PATENT DOCUMENTS

| | | | |
|---|---|---|---|
| EP | 0190543 | * | 6/1985 |
| WO | wo 92/03111 | * | 3/1992 |

* cited by examiner

Primary Examiner—Nicholas D. Lucchesi
Assistant Examiner—Huong Q. Pham
(74) Attorney, Agent, or Firm—John F. Salazar; Middleton Reutlinger

(57) ABSTRACT

An inexpensive and easy to use orthopedic splint made from a plurality of plastic ribs held together on a fabric sheath. The plurality of ribs is affixed to the sheath by adhesive or similar means at equal intervals across one surface of the sheath. The sheath can be designed to fit about a particular body section or it can be a generic rectangular unit. The ribs may be designed with perforations or other such similar weak areas so that the length of the splint may be shortened by breaking off and removing ends of the rib. Alternatively, the ribs may already have partitions so that breaking or cutting the ribs is not required. The ribs have apertures through which a cable tie or similar fastener is passed in order to secure the splint snugly to the injured appendage.

28 Claims, 8 Drawing Sheets

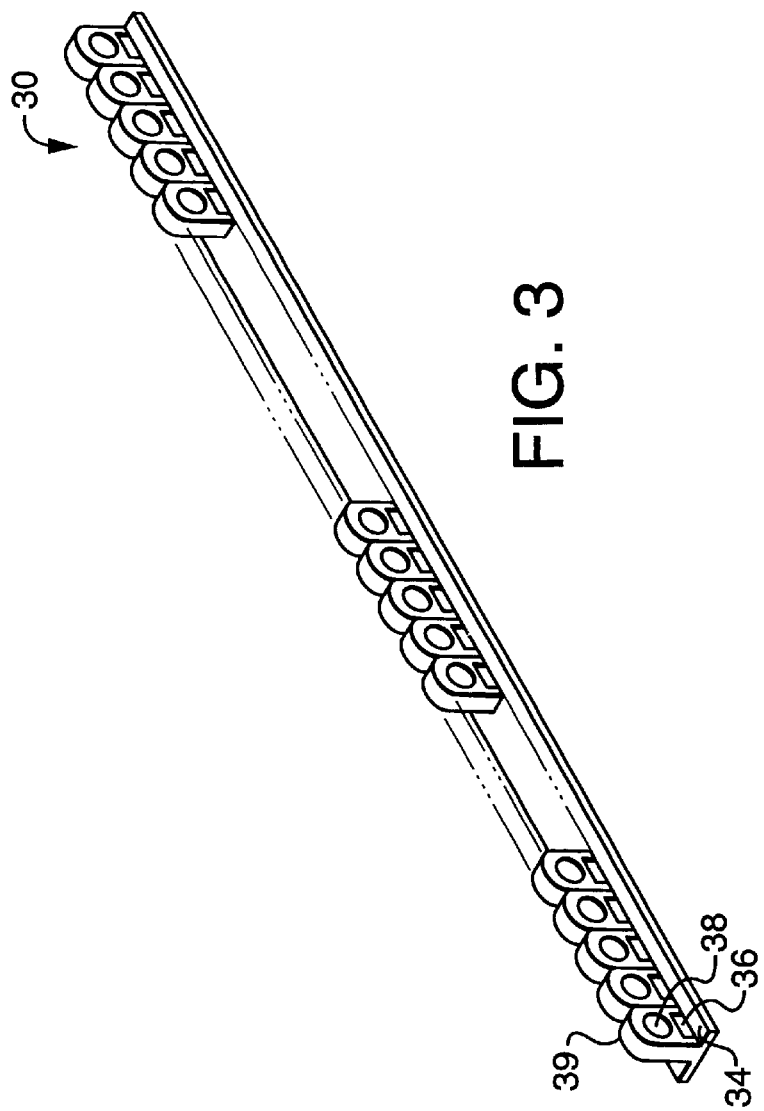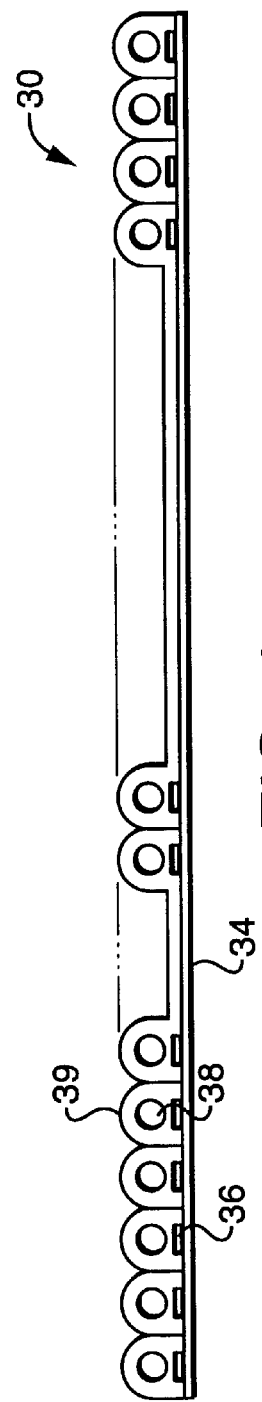

FLEXIBLE RIBBED SPLINT SYSTEM

BACKGROUND

The present invention relates to orthopedic medical products. More particularly, this invention relates to a versatile flexible splint system for immobilizing injured limbs and other body parts in order to facilitate healing.

Bone fractures, dislocations and connective tissue strains and tears are serious medical conditions that require immediate medical attention in order to prevent complications and unnecessary pain. Medical treatment for these injuries commonly includes immobilizing the damaged limb with a splint to promote healing of the bones in the proper orientation.

There are numerous types of splints that may be used to immobilize the injured limb. Traditional splints are composed of support boards secured against the injured body part with wrapped cloth. These splints are simple to use, but they provide only nominal support for the damaged limb. Formed plastic splints are designed to hold a limb in the proper splinted position. These splints provide better support than traditional splints, but it can be difficult to find a size that fits an individual properly. An improper fit can result in complications, such as failure to provide proper immobilization of the injured limb if the splint is too large, or restricted circulation to the damaged area if the splint is too small. Water-hardened or plaster splints are used extensively as long-term splinting materials in hospitals and physicians offices. These materials provide excellent support and are moldable to conform precisely to individual limb dimensions. However, if the splint is being applied outside a traditional medical facility, such as when splints are applied in the field by military medical personnel or by rescue workers, the lack of clean water for the preparation of plaster splints can be a problem. Further, the exothermic reaction associated with the hardening process can be uncomfortable against the patient's skin, and the resulting cast is bulky, heavy, and rigid. If post-injury swelling occurs, the cast must be cut off and a new one applied.

SUMMARY OF THE INVENTION

The present invention relates to a versatile flexible splint system for immobilizing injured limbs in order to facilitate healing. The splint system comprises a fabric sheath having a plurality of plastic ribs running longitudinally along the sheath. Adjustable plastic fasteners can be passed through apertures in the ribs to secure the sheath to the damaged limb. The ribs provide the support necessary to immobilize the limb.

Optionally, perforations or weak sections may be included in the ribs to permit them to be broken and removed from the fabric sheath. Alternatively, the ribs may be individual segments with short gaps in between each segment. This alleviates the need to break or cut the ribs. The sheath can then be shortened as needed to accommodate a variety of limb lengths.

SUMMARY OF THE FIGURES

FIG. 3 is a perspective view of one of the ribs used on the ribbed sheath shown in FIG. 1;

FIG. 4 is a side view of one of the ribs used on the ribbed sheath shown in FIG. 1;

DETAILED DESCRIPTION

The present invention relates to a versatile flexible splint system for immobilizing injured limbs in order to facilitate healing. The splint system includes a soft, lightweight, compact splint that can be quickly applied about a patient's limb, does not require clean water for preparation, and can be sized to accommodate limbs of different lengths and circumferences. A plurality of sizeable ties secure the splint around the patient's limb. The ties can be easily removed and replaced allowing the splint to be adjusted to compensate for swelling of a portion of the injured extremity without the need for removing the entire splint.

Figure 5:
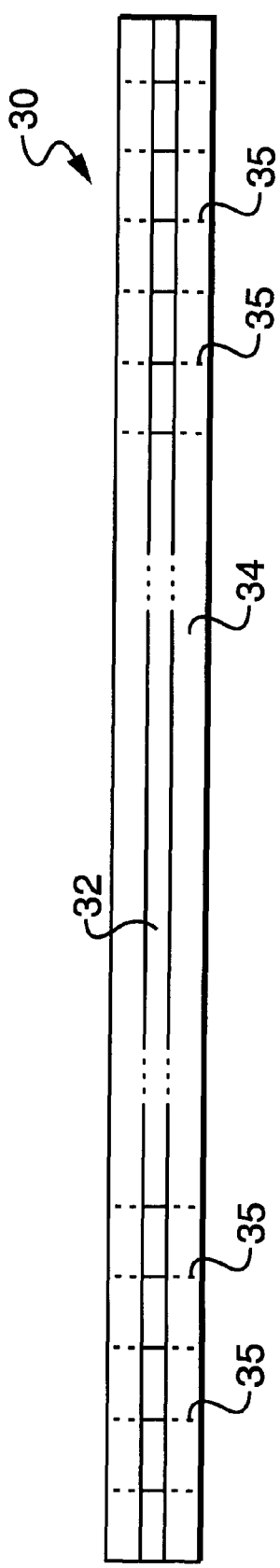
FIG. 5 is a top view of one of the ribs used on the ribbed sheath shown in FIG. 1.
Figure 6:
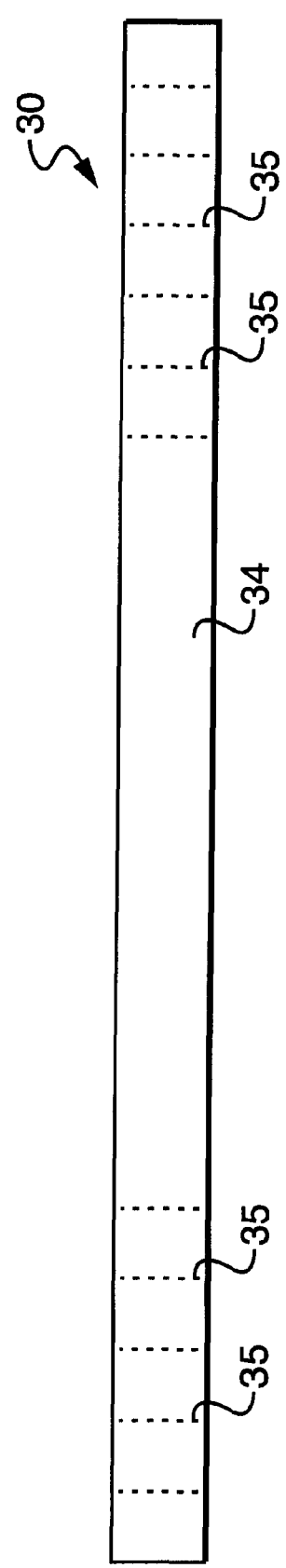
FIG. 6 is a bottom view of one of the ribs used on the ribbed sheath shown in FIG. 1.
Figure 7:
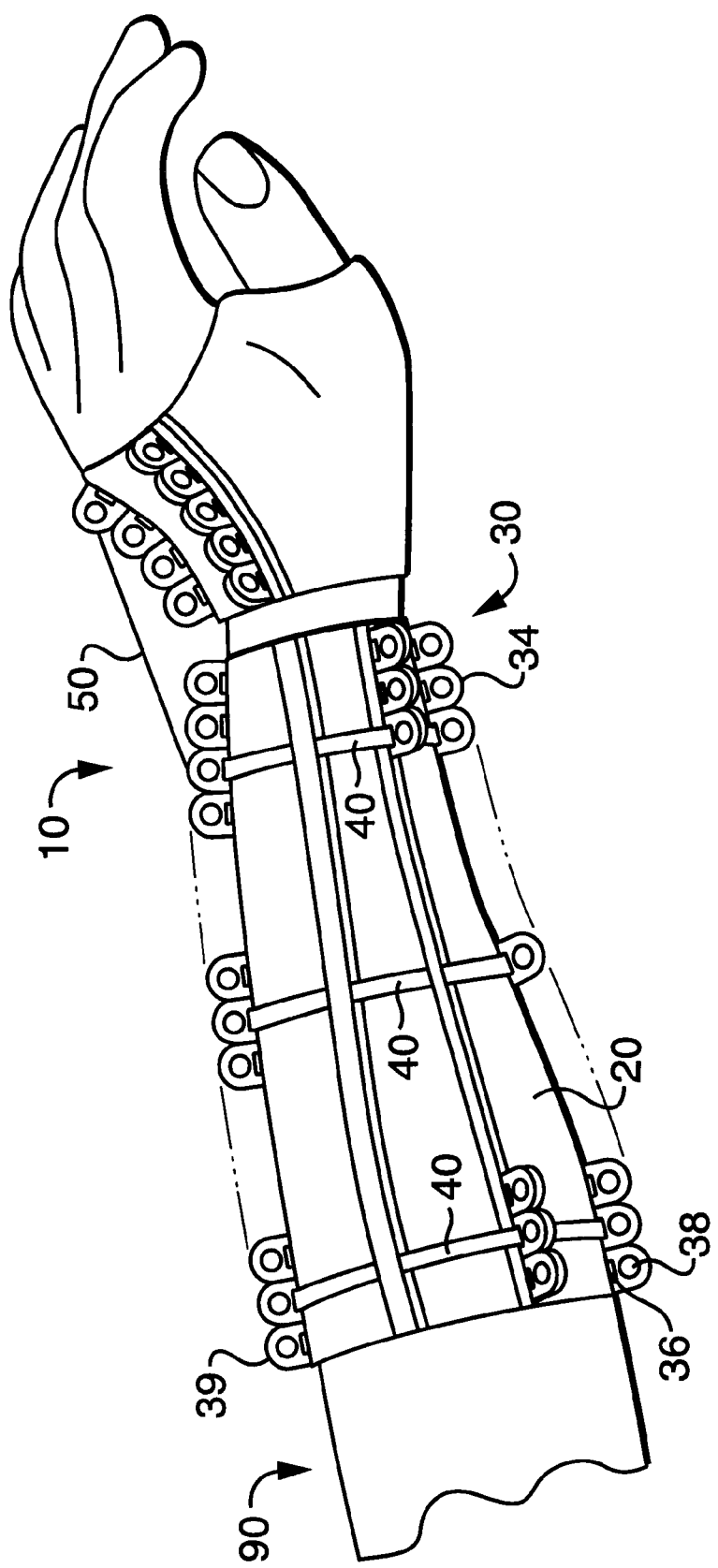
FIG. 7 is the splint system of FIG. 1 shown positioned about a person's arm.

As shown in FIGS. 1–11, the splint system 10 of the present invention comprises a splint 20 having a fabric sheath 22 with a plurality of plastic ribs 30 running longitudinally along the sheath 20. A plurality of adjustable plastic fasteners 40 can be used to secure the splint 20 to the damaged limb 90. Optionally, as shown in FIG. 7, one or more stays 50 may be used to retain the muscles associated with the damaged limb 90 at the desired angle to ensure proper healing of the limb 90 without causing permanent damage to the mobility of the limb 90.

Referring to FIGS. 1–6, the splint 20 comprises the fabric sheath 22 and the ribs 30. The sheath 22 can be made from any woven or non-woven material which can be wrapped about the damaged limb 90 and can be cut to size. Because the sheath 22 is intended to make direct contact with a patient's skin, it is recommended that the sheath 22 be made from a soft, breathable material such as linen, lightweight cotton, gauze, lightweight poly/cotton, or a similar material that will be comfortable and non-irritating against the patient's skin. Optionally, the sheath 22 may include markings, such as length designations or rib positioning templates.

Figure 1:
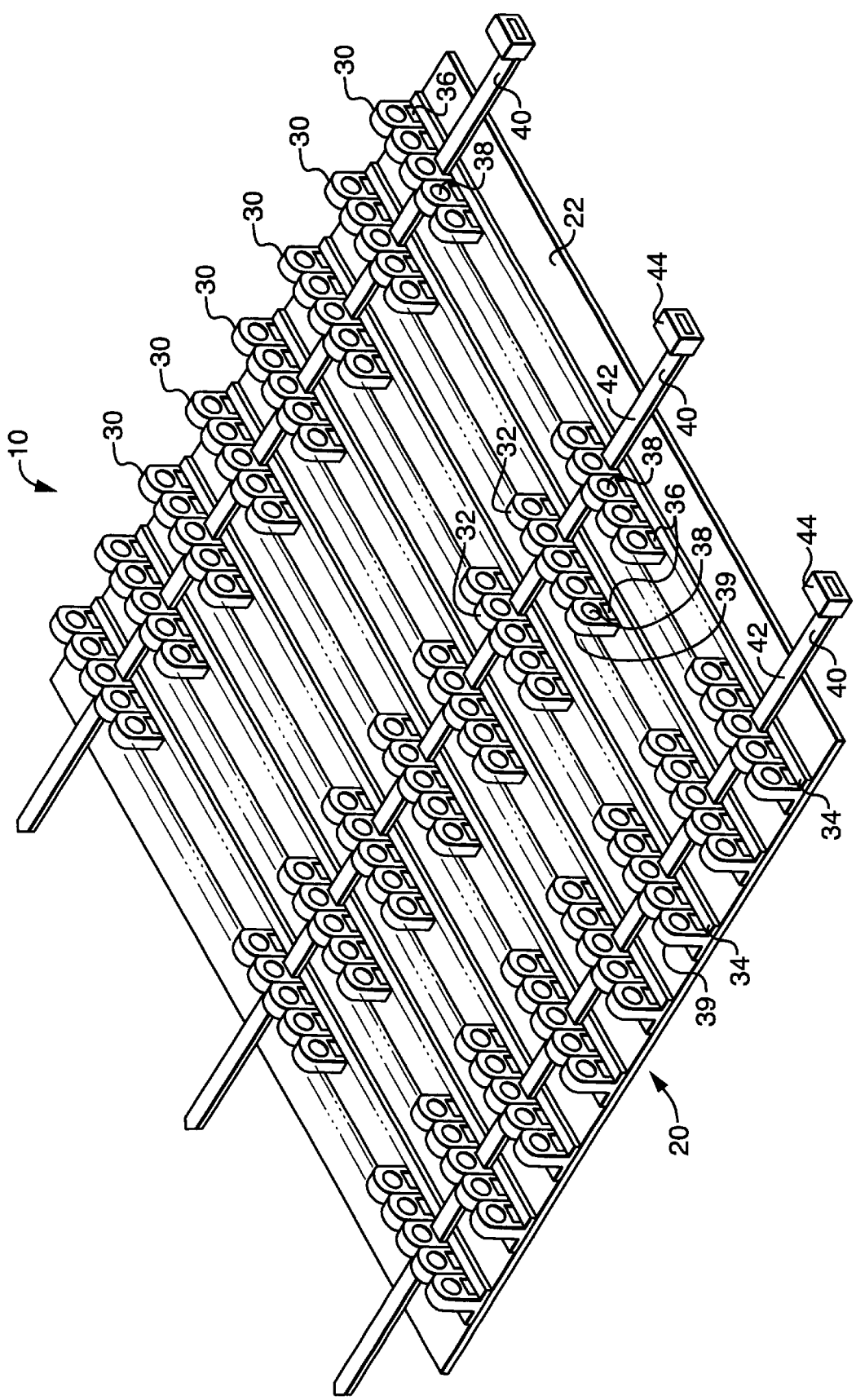
FIG. 1 is a perspective view of a splint system made in accordance with the present invention.
Figure 2:
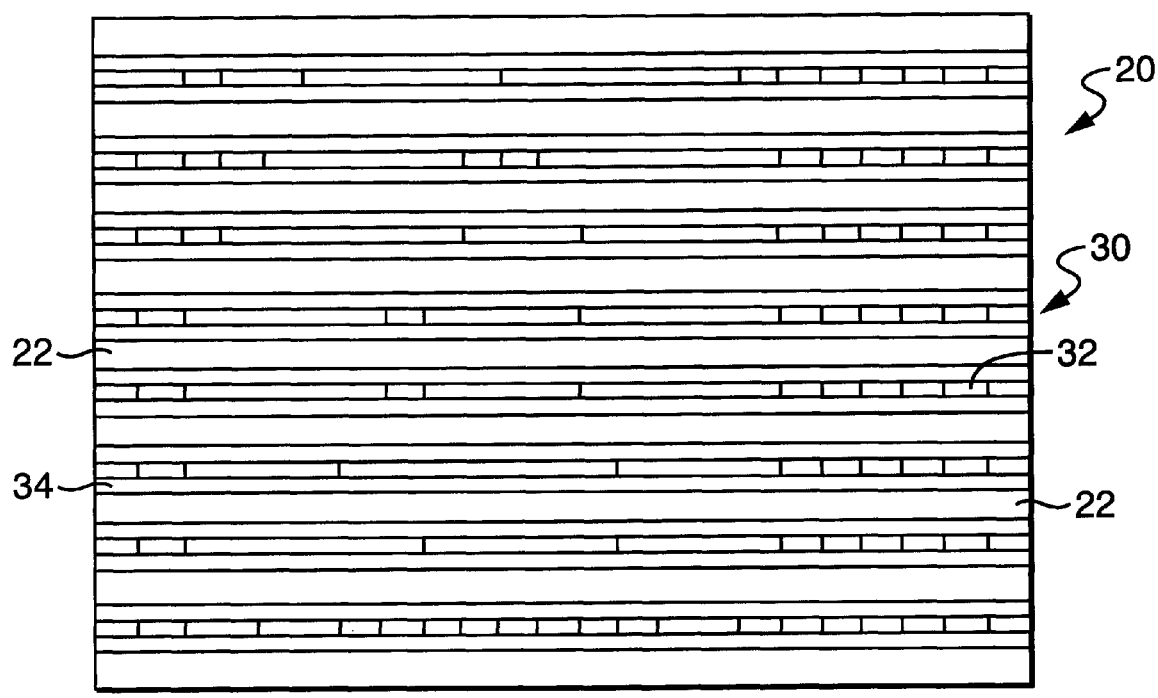
FIG. 2 is a top view of the ribbed sheath shown in FIG. 1.

The ribs 30 include a plurality of fins 32 secured to an essentially flat backbone 34. In one embodiment shown, and particularly as shown in FIGS. 1 and 2, the ribs 30 are essentially evenly spaced along the fabric sheath 22, with about ½" of fabric being exposed between any two neighboring backbones 34. Alternatively, the ribs 30 may be irregularly spaced or may have a greater or lesser amount of fabric sheath 22 between the backbones 34 as desired by the user.

Figure 8:
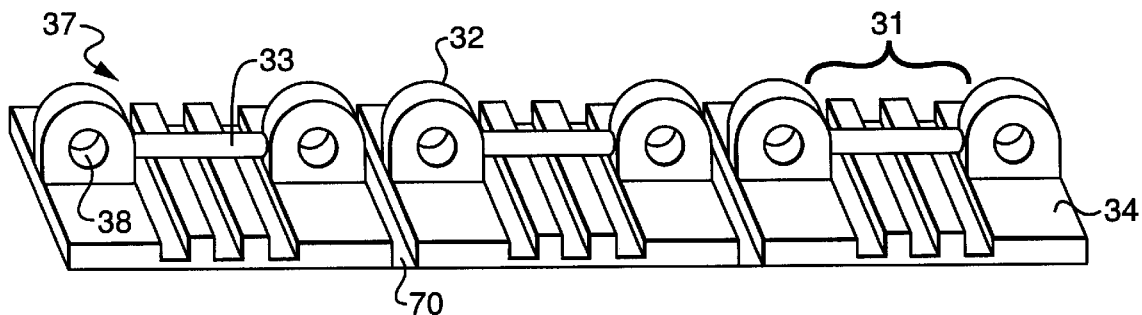
FIG. 8 is a perspective view of another embodiment of one of the ribs used on the ribbed sheath shown in FIG. 1.

In one embodiment shown, the fins 32 run along the entire length of the backbone 34. Each fin 32 includes a pair of apertures 36, 38. As shown in FIGS. 3 and 4, the first aperture 36 is positioned essentially adjacent to the backbone 34, and in the embodiment shown, is rectangular in shape. The first aperture 36 is intended to receive the fastener 40 to secure the splint 20 to the damaged limb 90. Thus, the shape of the aperture 36 may vary as necessary to accommodate the selected fastener 40. The second aperture 38 is positioned near an end 39 of the fin 32, and in the embodiment shown, is essentially round in shape. The second aperture 38 is intended to receive the stay 50, and the shape of the aperture 38 may vary as necessary to accommodate the selected stay 50. As shown in FIGS. 5 and 6, the backbone 34 of the rib 30 optionally includes lines of perforation 35. The perforations 35 allow the user to break the rib 30 to the desired length and then to trim the sheath 22 to provide the best fit about the damaged limb 90. Alternatively, the ribs can comprise short rib units 37 aligned in parallel rows with narrow breaches 70 between each segment as shown in FIG. 8. The breaches 70 are narrow enough that the ribs still provide stability and support to the injured body part, but wide enough to permit a cutting device to shear the fabric sheath 22 at the breach 70. This arrangement alleviates the need to break or cut the ribs in order to shorten and fit the splint properly to the patient.

Figure 9:
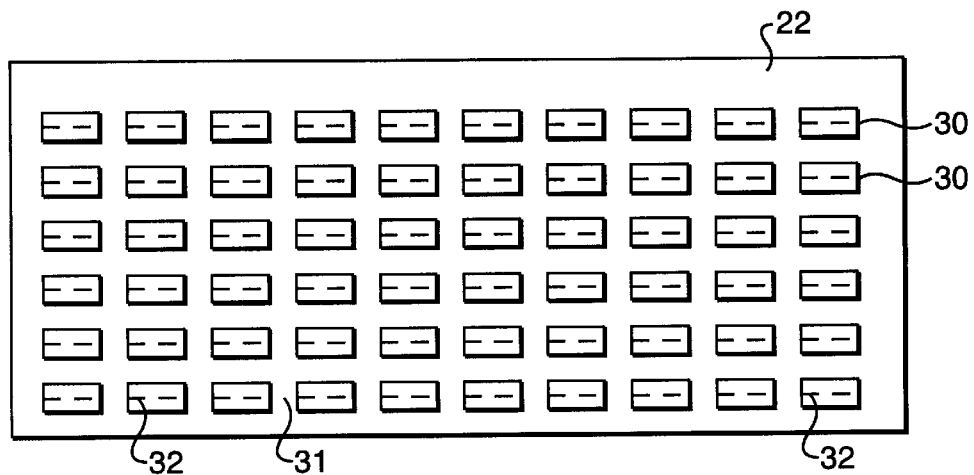
FIG. 9 is a top view of another embodiment of the ribbed sheath.

In another embodiment, as shown in FIG. 9, the fins 32 run the length of the backbone, however there are gaps 31 between some of the fins 32. The gaps 31 may be positioned with one or more fins 32 between each gap 31 as may be required. Each fin 32 has one aperture 38, rather than two. The gap 31 is intended to receive the fastener 40, rather than a second aperture. The gaps 31 may also have one or more ridges 33 that extend upward from the backbone 34. The ridges 33 serve two functions. First, they disperse the downward force of the fastener 40 on the rib 30 across a broader surface. Second, the ridges 33 raise the fastener 40 slightly above the surface of the splint 20, permitting a user to more easily slip a finger or instrument between the splint 20 and fastener 40 as needed to adjust or quickly cut the fastener 40.

The ribs 30 may also be supplied to the user separate from the sheath 22. The ribs 30 may have a pre-applied adhesive on the side of the backbone that would face the sheath 22, or a separate adhesive may be supplied to the user. The user could then position the ribs 30 on the sheath 22 to best accommodate the damaged limb 90. Alternatively, the user may position the ribs 30 along the pre-printed markings or templates on the sheath 22.

As shown in FIG. 1, the splint system 10 of the present invention also includes one or more adjustable plastic fasteners 40 which can be used to secure the splint 20 to the damaged limb 90. The fasteners 40 include a semi-rigid plastic strip 42 with a retention device 44. The plastic strip 42 is passed through the first apertures 36 of neighboring ribs 30. The strip 42 is then passed through the retention device 44 of the respective fastener 40 and tightened by the desired amount. The retention device 44 grabs or catches the strip 42 preventing the strip 42 from loosening, similar to the action of a common cable tie.

Optionally, as shown in FIG. 7, the splint system of the present invention may include one or more stays 50 to retain the muscles associated with the damaged limb 90 at the desired angle to ensure proper healing of the limb 90 without causing permanent damage to the mobility of the limb 90. The stays 50 may have a variety of designs as desired by the user. For example, the stay 50 may be a relatively short plastic strip with locking means, such as nubs or buttons attached to either end of the strip. The nubs should be sized to fit through and matingly engage the second aperture 38 of the fins 32. Alternatively, the stay 50 may be a plastic fastener 40 with the strip 42 threaded through the second apertures 38 of the fins and then held by the retention device 44.

Figure 10:
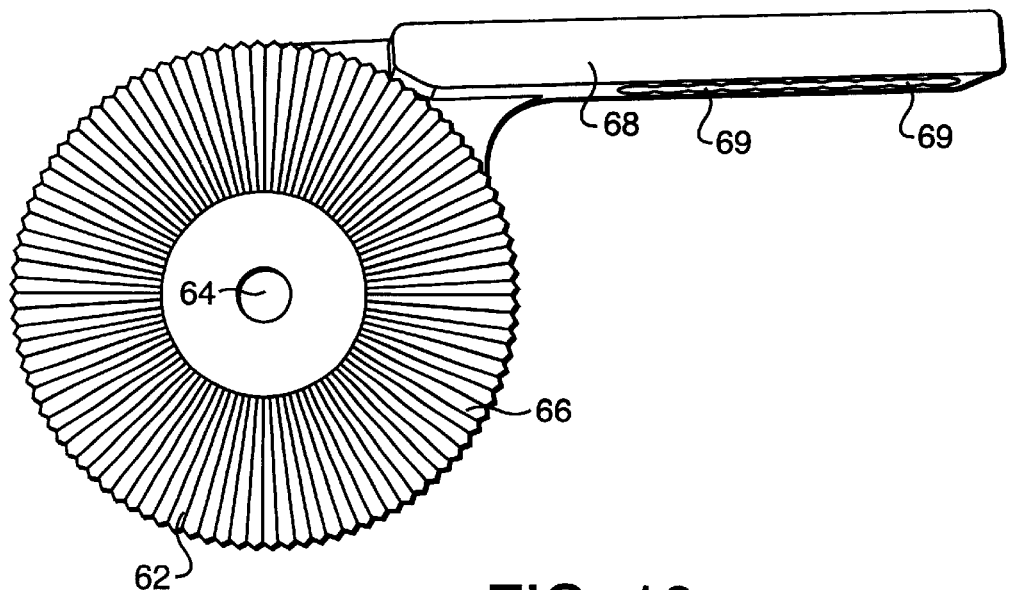
FIG. 10 is a side view of an embodiment of one of the mated members of the locking hinge.
Figure 11:
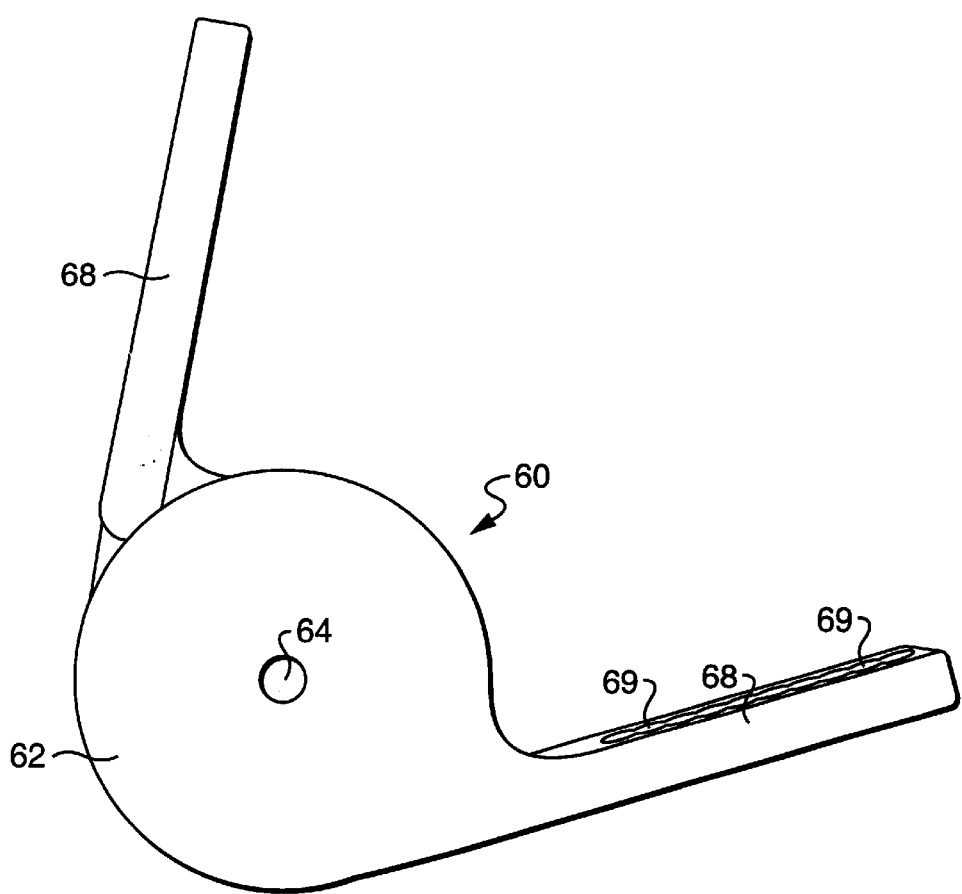
FIG. 11 is a side view of an embodiment of the assembled locking hinge.
Figure 12:
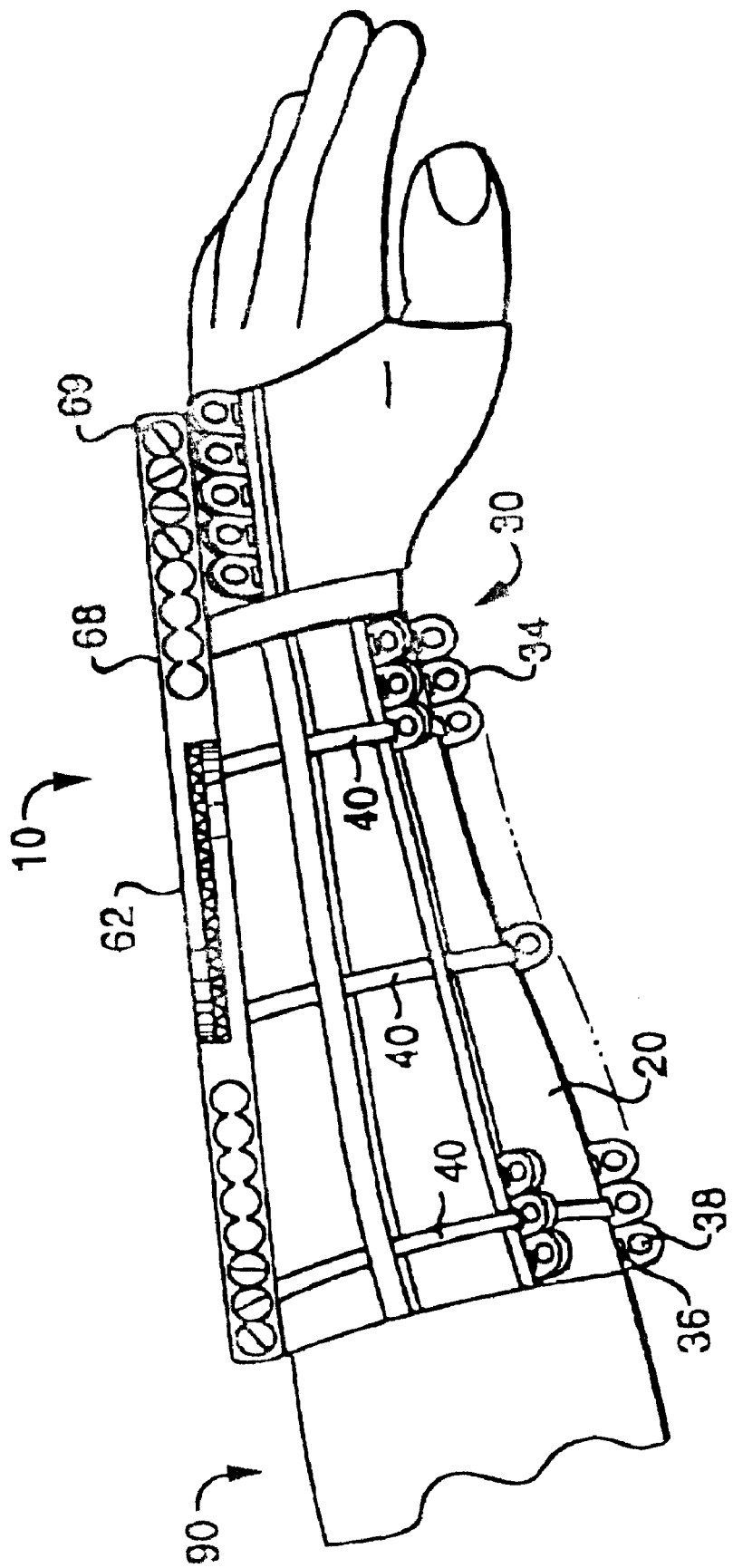
FIG. 12 is a splint system of FIG. 7 shown positioned about a person's arm having a locking hinge connected thereto.

Alone or in combination with the stays 50, the splint system of the present invention may incorporate a locking hinge 60 at a joint to further provide stability and rigidity for stabilizing a limb in a particular position. As shown in FIGS. 10 and 11, the embodiment of the locking hinge 60 may comprise a two part hinge system, each of the first and second mated members (FIG. 10) comprising a central body 62 having a generally circular design. At the center of the central body 62 is a central opening 64 sized to accept a fastening means, such as a screw or rivet that permits rotatable connection of the two halves of the locking hinge 60. Radiating outward from the central opening is a plurality of radial ridges 66. The radial ridges 66 lockingly engage complementary radiating ridges 66 on the other half of the locking hinge 60. Extending from the central body 62 is a fastening arm 68 having a plurality of interlinked openings 69 for securing the locking hinge 60 with a fastening means such as a screw or rivet to an aperture 38 on a fin 32, as shown in FIG. 12. FIG. 11 shows the assembled locking hinge 60.

In use, the limb is positioned as desired with the splint in place and each half of the locking hinge 60 positioned so that the radial ridges 66 lockingly engage and secure the fastening arms 68 at the angle desired to secure the limb properly. The locking hinge 60 is affixed to the splint 20 using a fastening means securing the fastening arm 68 to a fin 32. Another fastening means through the central opening 64 locks the two halves of the locking hinge 60 at the desired angle. The locking hinge 60 can be constructed so that only one size and type of fastening means is required to lock the two halves of the locking hinge 60 together and attach the fastening arms 68 to the splint 20.

The splint system 10 of the present invention is ideally suited for use in field situations where time is of the essence and materials and expertise are limited. The splint system 10 is easy to use, is lightweight and compact for transporting, does not require water for setting the materials, and can easily be sized and re-adjusted to accommodate post-injury swelling. For example, if the damaged limb 90 swells at a particular section, one or more fasteners 40 in the swollen region may be cut away and replaced with new fasteners 40 without the need to remove the entire splint 20.

From a reading of the above, one with ordinary skill in the art should be able to devise variations to the inventive features. For example, a variety of fasteners may be used to secure the splint to the damaged limb, and the apertures may vary in shape to better accommodate the selected fastener. Further, a plurality of splints, sheaths, ribs or a combination thereof, may be used interchangeably to best stabilize the damaged limb. These and other variations are believed to fall within the spirit and scope of the present invention.

What is claimed is:

1. A versatile splint for immobilizing injured body parts, comprising:
   a fabric sheath;
   a plurality of ribs having a flat backbone with a bottom surface and a top surface, each of said plurality of ribs adhered to said sheath at said bottom surface, each of said plurality of ribs having a plurality of fins projecting upward from said top surface, said fins having at least one aperture through each of said fins;
   a locking hinge affixed to said at least one aperture in at least a first fin and a second fin of said plurality of fins, said locking hinge having a first member and a second member, said first member and said second member each having a central body and a fastening arm extending from said central body, said fastening arm having a plurality of interlinked adjustable openings through said fastening arm for affixing said locking hinge to said plurality of fins, said first and second members lockingly engaged at said central body; and one or more fasteners having an elongated strip, said elongated strip passing through said apertures of two or more of said fins to affix said splint to and immobilize said injured body part.

2. The versatile splint of claim 1, said fabric sheath being a material selected from the group consisting of linen, cotton, gauze and lightweight poly/cotton.

3. The versatile splint of claim 2, said fabric sheath further comprising markings on a surface of said fabric sheath.

4. The versatile splint of claim 3, said markings being length designations indicating where the sheath can be cut by a user in order to provide a proper fit for a patient.

5. The versatile splint of claim 1, said ribs being arranged longitudinally along said sheath in a parallel pattern.

6. The versatile splint of claim 5, said ribs being evenly spaced apart from each other.

7. The versatile splint of claim 1, said plurality of fins each having a first aperture positioned adjacent said flat backbone and a second aperture at an upper end of said fin, wherein said first aperture is shaped so as to permit passage of said strip through said first aperture.

8. The versatile splint of claim 7, further comprising at least one stay for retaining a body part in a particular configuration by affixing each of a first end and a second end of said stay to different said second apertures.

9. The versatile splint of claim 1, said plurality of fins each having one aperture and said plurality of fins being arranged along said ribs so that a breach is formed between two or more of said plurality of fins.

10. The versatile splint of claim 9, having a gap between two or more of said plurality of fins, said gap having a width great enough to accommodate said strip within said gap.

11. The versatile splint of claim 10, said gap further comprising ridges extending upward from said top surface of said ribs in said gap.

12. The versatile splint of claim 1, said fastener further comprising a retention device that holds said strip at a fixed tension against said splint.

13. The versatile splint of claim 1, said flat backbone having a plurality of perforation lines through said flat backbone spaced at regular distances so as to permit sizing of said ribs by breaking off a length of said rib at said perforation line.

14. The versatile splint of claim 1, said plurality of ribs being segments with short spaces between each of said segments so as to permit sizing of said splint by cutting said fabric sheath to a proper size, including easily cutting said sheath at regions within said short spaces.

15. The versatile splint of claim 1, said central body having a plurality of radial ridges extending outward from a central opening, wherein said first and second members are lockingly engaged by mating said radial ridges and holding said first and second members together with a fastener inserted through said central opening.

16. A customizable splint for immobilizing a variety of different injured body parts, comprising:

a fabric sheath;

a plurality of ribs adhered to said sheath, said plurality of ribs being a plurality of individual rib units in alignment and having a short breach between each of said rib units so as to permit sizing of said splint by cutting said sheath at any of said breaches;

a locking hinge affixed to said plurality of ribs, said locking hinge having a first member and a second member, said first member and said second member each having a central body and a fastening arm extending from said central body, said fastening arm having a plurality of interlinked adjustable openings through said fastening arm for affixing said locking hinge to said plurality of ribs, said first and second members lockingly engaged at said central body; and one or more fasteners having an elongated strip and a retention device, said retention device affixing said elongated strip to said splint so as to immobilize said injured body part.

17. The customizable splint of claim 16, said plurality of rib units each having at least one fin projecting upward from a surface of said rib unit, said fin having at least one aperture through said fin.

18. The customizable splint of claim 17, said plurality of rib units each having a first fin and a second fin and a gap between said first fin and said second fin, said gap width being large enough to accommodate said elongated strip within said gap.

19. The customizable splint of claim 18, said gap further comprising ridges extending upward from said surface of said rib unit in said gap.

20. The customizable splint of claim 16, said fabric sheath being a material selected from the group consisting of linen, cotton, gauze and lightweight poly/cotton.

21. The customizable splint of claim 20, said fabric sheath further comprising markings on a surface of said fabric sheath.

22. The customizable splint of claim 21, said markings being length designations indicating where the sheath can be cut by a user in order to provide a proper fit for a patient.

23. The customizable splint of claim 16, said ribs being arranged longitudinally along said sheath in a parallel pattern.

24. The customizable splint of claim 17, further comprising at least one stay for retaining a body part in a particular configuration by affixing each of a first end and a second end of said stay to different of said apertures.

25. The customizable splint of claim 16, said central body having a plurality of radial ridges extending outward from a central opening, wherein said first and second members are lockingly engaged by mating said radial ridges and holding said first and second members together with a fastener inserted through said central opening.

26. The customizable splint of claim 16, said rib units being frangibly connected at said short breach.

27. The customizable splint of claim 26, said frangible connection being a plurality of perforation lines through said rib.

28. The customizable splint of claim 26, said fins each having a first aperture positioned at a lower end of said fin and a second aperture at an upper end of said fin, wherein said first aperture is shaped so as to permit passage of said strip through said first aperture.

* * * * *